(12) United States Patent
Maurer, Jr. et al.

(10) Patent No.: US 8,971,490 B2
(45) Date of Patent: *Mar. 3, 2015

(54) CONTROLLING X-RAY IMAGING BASED ON TARGET MOTION

(75) Inventors: Calvin R. Maurer, Jr., Mountain View, CA (US); Sohail Sayeh, San Ramon, CA (US); Matthew A. Core, San Jose, CA (US)

(73) Assignee: Accuray Incorporated, Sunnyvale, CA (US)

( * ) Notice: Subject to any disclaimer, the term of this patent is extended or adjusted under 35 U.S.C. 154(b) by 184 days.

This patent is subject to a terminal disclaimer.

(21) Appl. No.: 13/359,365

(22) Filed: Jan. 26, 2012

(65) Prior Publication Data
US 2012/0121068 A1   May 17, 2012

Related U.S. Application Data

(63) Continuation of application No. 12/558,489, filed on Sep. 11, 2009, now Pat. No. 8,130,907.

(60) Provisional application No. 61/096,722, filed on Sep. 12, 2008.

(51) Int. Cl.
*A61N 5/10* (2006.01)
*A61B 6/12* (2006.01)
*A61B 6/00* (2006.01)
(Continued)

(52) U.S. Cl.
CPC ... *A61B 6/12* (2013.01); *A61B 6/00* (2013.01); *A61B 6/486* (2013.01); *A61B 6/488* (2013.01); *A61B 6/5217* (2013.01); *A61B 6/541* (2013.01); *A61N 5/1049* (2013.01); *A61B 5/1114* (2013.01); *A61B 8/0833* (2013.01); *A61B 19/5244* (2013.01); *A61B 2019/5251* (2013.01); *A61B 2019/5255* (2013.01); *A61N 2005/1061* (2013.01)
USPC ............................................. 378/65; 378/95

(58) Field of Classification Search
CPC .. A61N 5/1037; A61N 5/1049; A61N 5/1064
USPC .................................................... 378/95, 65
See application file for complete search history.

(56) References Cited

U.S. PATENT DOCUMENTS

| 4,409,615 A | 10/1983 | McMann et al. |
| 4,942,596 A | 7/1990 | Eberhard et al. |

(Continued)

FOREIGN PATENT DOCUMENTS

| EP | 1332721 A1 | 8/2003 |
| WO | 0024467 A1 | 5/2000 |
| WO | 2004008969 A2 | 1/2004 |

OTHER PUBLICATIONS

European Search Report for Europe Patent Application No. 09813381.2, mailed Jan. 24, 2013, 5 pages.

(Continued)

*Primary Examiner* — Glen Kao
(74) *Attorney, Agent, or Firm* — Lowenstein Sandler LLP

(57) ABSTRACT

An image guided treatment is performed to treat a target. To perform the image guided treatment, measurement data indicative of target motion is acquired. A timing of one or more x-ray images is determined based on the measurement data. Treatment may be performed on the target using the position of the target.

6 Claims, 10 Drawing Sheets

(51) Int. Cl.
*A61B 5/11* (2006.01)
*A61B 8/08* (2006.01)
*A61B 19/00* (2006.01)

(56) References Cited

U.S. PATENT DOCUMENTS

| | | | |
|---|---|---|---|
| 5,187,730 | A | 2/1993 | Fujihara |
| 5,204,533 | A | 4/1993 | Simonet |
| 5,205,289 | A | 4/1993 | Hardey et al. |
| 5,207,223 | A | 5/1993 | Adler |
| 5,230,338 | A | 7/1993 | Allen et al. |
| 5,319,696 | A | 6/1994 | Abdel-Malek et al. |
| 5,398,684 | A | 3/1995 | Hardy |
| 5,427,097 | A | 6/1995 | Depp |
| 5,471,516 | A | 11/1995 | Nunan |
| 5,724,403 | A | 3/1998 | Siochi et al. |
| 5,917,883 | A | 6/1999 | Khutoryansky et al. |
| 6,148,060 | A | 11/2000 | Collins et al. |
| 6,219,403 | B1 | 4/2001 | Nishihara |
| 6,385,286 | B1 | 5/2002 | Fitchard et al. |
| 6,504,893 | B1 | 1/2003 | Flohr et al. |
| 6,731,970 | B2 | 5/2004 | Schlossbauer et al. |
| 7,421,061 | B2 | 9/2008 | Boese et al. |
| 7,508,913 | B2 | 3/2009 | Boese et al. |
| 8,130,907 | B2 * | 3/2012 | Maurer et al. ............ 378/65 |
| 2002/0085672 | A1 | 7/2002 | Ganin et al. |
| 2002/0191741 | A1 | 12/2002 | Brendler et al. |
| 2003/0002621 | A1 * | 1/2003 | Hughes et al. ............ 378/65 |
| 2003/0048868 | A1 | 3/2003 | Bailey et al. |
| 2003/0215120 | A1 | 11/2003 | Uppaluri et al. |
| 2004/0044279 | A1 | 3/2004 | Lewin et al. |
| 2004/0092815 | A1 | 5/2004 | Schweikard et al. |
| 2004/0120452 | A1 | 6/2004 | Shapiro et al. |
| 2005/0053196 | A1 | 3/2005 | Mostafavi |
| 2005/0054916 | A1 * | 3/2005 | Mostafavi ............ 600/427 |
| 2005/0058248 | A1 | 3/2005 | Klingenbeck-Regn |
| 2005/0201510 | A1 | 9/2005 | Mostafavi |
| 2005/0276377 | A1 | 12/2005 | Carol |
| 2006/0008174 | A1 | 1/2006 | Avinash et al. |
| 2006/0074292 | A1 | 4/2006 | Thomson et al. |
| 2006/0074299 | A1 | 4/2006 | Sayeh |
| 2006/0133573 | A1 | 6/2006 | Wong et al. |
| 2007/0015991 | A1 | 1/2007 | Fu et al. |
| 2007/0041494 | A1 * | 2/2007 | Ruchala et al. ............ 378/65 |
| 2007/0041499 | A1 * | 2/2007 | Lu et al. ............ 378/65 |
| 2007/0076846 | A1 | 4/2007 | Ruchala et al. |
| 2007/0078306 | A1 | 4/2007 | Allison et al. |
| 2007/0100233 | A1 | 5/2007 | Thomson |
| 2007/0165781 | A1 | 7/2007 | Aslund |
| 2007/0189455 | A1 | 8/2007 | Allison |
| 2007/0270689 | A1 | 11/2007 | Lothert |
| 2008/0031404 | A1 | 2/2008 | Khamene et al. |
| 2009/0041189 | A1 | 2/2009 | Allison |
| 2010/0067660 | A1 | 3/2010 | Maurer, Jr. et al. |
| 2012/0008734 | A1 | 1/2012 | Thomson et al. |

OTHER PUBLICATIONS

Chen, Q-S. et al. (Sep. 2001). "Fluoroscopic Study of Tumor Motion due to Breathing: Facilitating Precise Radiation Therapy for Lung Cancer Patients", American Association of Physical Medicine, Medical Physics 28(9) 1850-1856.

PCT International Search Report and Written Opinion of the International Searching Authority, PCT/US07/04124, International Filing Date Feb. 13, 2007, mailed Mar. 4, 2008.

Coste-Maniere, E., "Robotic whole body stereotactic radiosurgery: clinical advantages of the CyberKnife® integrated system", The International Journal of Medical Robotics +Computer Assisted Surgery, 2005, www.robacpublicationsmm, 12 pages.

Penney, G.P. et al., "A Comparison of Similarity Measures for Use in 2-D-3-D Medical Image Registration", IEEE Transactions on Medical Imaging, vol. 17, No. 4, Aug. 1998, pp. 589-595.

Tapiovaara, M.J. et al., "Evaluation of Image Quality in Fluroscopy by Measurements and Monte Carlo Calculations", Phys. Med. Biol. 40 (1995) Copyright 1998IOP Publishing LTD, pp. 589-607.

PCT International Preliminary Report on Patentability, PCT/US2007/004124, International Filing Date Feb. 13, 2007, mailed Aug. 28, 2008.

Accuray Incorporated Office Action for U.S. Appl. No. 11/354,411 mailed May 14, 2009.

PCT International Search Report and The Written Opinion of the International Searching Authority, PCT/US09/05149, filed Sep. 11, 2009, mailed Nov. 9, 2009, 13 pages.

U.S. Appl. No. 12/250,262, Final Office Action mailed Dec. 1, 2009.
U.S. Appl. No. 12/250,262, Office Action mailed Apr. 22, 2010.
U.S. Appl. No. 12/250,262, Office Action mailed Dec. 8, 2010.
U.S. Appl. No. 12/250,262, Final Office Action mailed Jun. 13, 2011.
Non-final Office Action mailed Jun. 14, 2011, for U.S. Appl. No. 12/558,489, filed Sep. 9, 2011, 12 pages.
Notice of Allowance mailed Oct. 27, 2011, for U.S. Appl. No. 12/558,489, filed Sep. 9, 2011, 9 pages.

* cited by examiner

CONTROLLING X-RAY IMAGING BASED ON TARGET MOTION

RELATED APPLICATIONS

This application is a continuation of U.S. patent application Ser. No. 12/558,489, filed on Sep. 11, 2009, which claims priority to U.S. Provisional Patent Application No. 61/096,722 filed Sep. 12, 2008, which are hereby incorporated by reference in their entirety.

TECHNICAL FIELD

Embodiments of the present invention relate to the field of image guided treatment and, in particular, to a system for determining a timing of diagnostic x-ray images based on measurement data indicative of target motion.

BACKGROUND

Radiosurgery and radiotherapy systems are radiation treatment systems that use external radiation beams to treat pathological anatomies (e.g., tumors, lesions, vascular malformations, nerve disorders, etc.) by delivering a prescribed dose of radiation (e.g., x-rays) to the pathological anatomy while minimizing radiation exposure to surrounding tissue and critical anatomical structures (e.g., the spinal cord). Both radiosurgery and radiotherapy are designed to necrotize the pathological anatomy while sparing healthy tissue and the critical structures. Radiotherapy is characterized by a low radiation dose per treatment, and many treatments (e.g., 30 to 45 days of treatment). Radiosurgery is characterized by a relatively high radiation dose in one, or at most a few, treatments.

In both radiotherapy and radiosurgery, the radiation dose is delivered to the site of the pathological anatomy from multiple angles. As the angle of each radiation beam is different, each beam can intersect a target region occupied by the pathological anatomy, while passing through different regions of healthy tissue on its way to and from the target region. As a result, the cumulative radiation dose in the target region is high and the average radiation dose to healthy tissue and critical structures is low. Radiotherapy and radiosurgery treatment systems can be classified as frame-based or image-guided.

One challenge facing the delivery of radiation to treat pathological anatomies, such as tumors or lesions, is identifying the location of the target (i.e. tumor location within a patient). The most common technique currently used to identify and target a tumor location for treatment involves a diagnostic x-ray or fluoroscopy system to image the patient's body to detect the position of the tumor. This technique assumes that the tumor does not move appreciably over the course of a treatment.

Current methods track and account for tumor motion during delivery of radiation treatment using multiple diagnostic x-rays over the course of treatment, as the skilled artisan will appreciate. In these current methods and systems a user specifies how many radiation treatment beams should be delivered between each diagnostic x-ray image. In such systems, delivery of beams can vary drastically in time duration. For example, imaging every 3 beams could result in one pair of images taken 10 seconds apart, interleaved by 3 short beams, followed by an image taken more than a minute later after 3 long beams. However, the tumor may have moved between the two diagnostic x-ray images, thereby resulting in less than desired accuracy of delivery of treatment radiation beams to the target, and a larger than desired radiation dose delivered to healthy tissue surrounding the target.

BRIEF DESCRIPTION OF THE DRAWINGS

The present invention is illustrated by way of example, and not by way of limitation, in the figures of the accompanying drawings.

DETAILED DESCRIPTION

Figure 1:
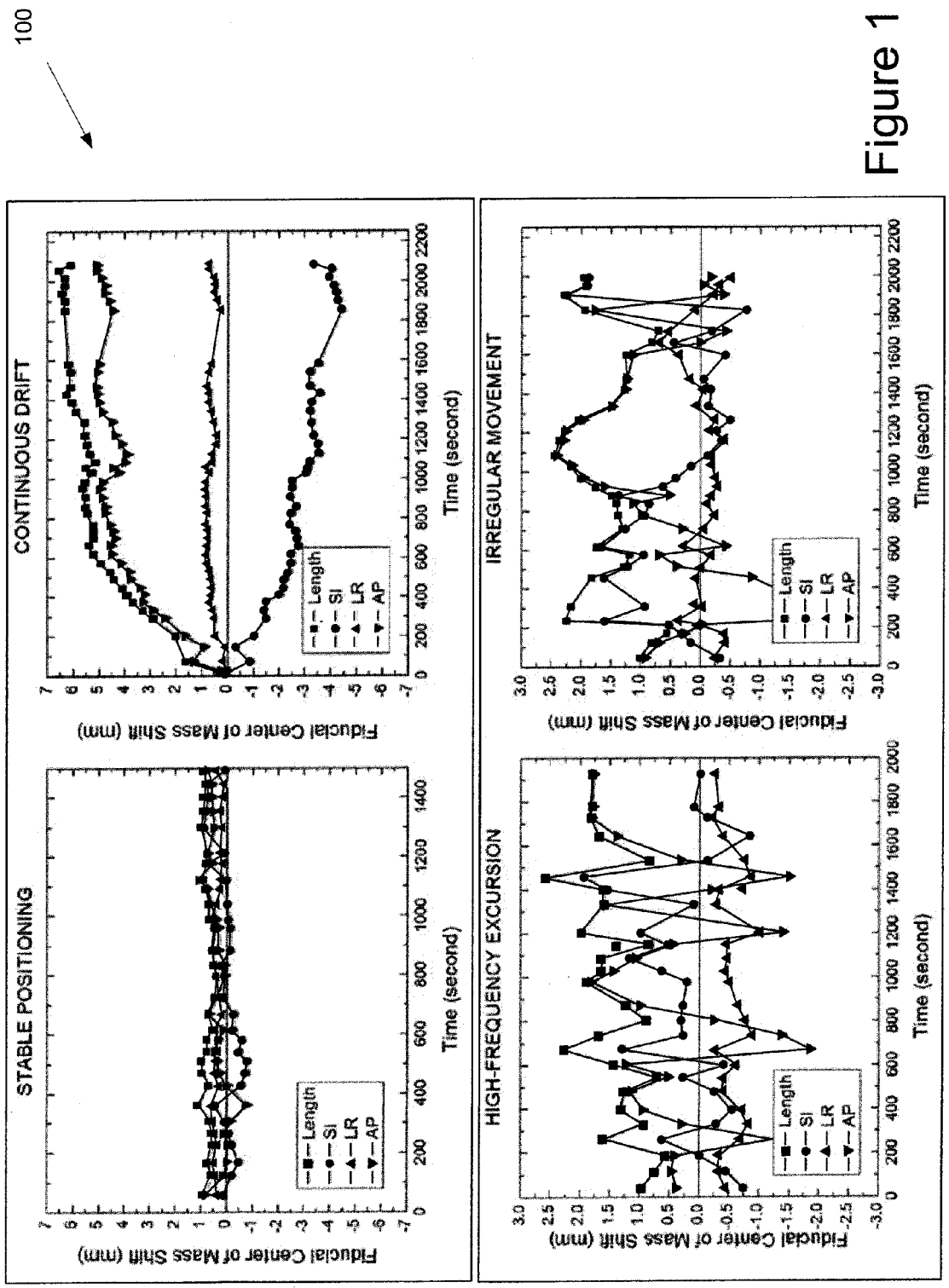
FIG. 1 illustrates graphs showing example prostate movement during a radiation treatment session.

Described herein is a method and apparatus for providing image guidance for patient treatment. The following description sets forth numerous specific details such as examples of specific systems, components, methods, and so forth, in order to provide an understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth are merely exemplary. Particular implementations may vary from these exemplary details and still be contemplated to be within the spirit and scope of the present invention.

The term "x-ray image" as used herein may mean a visible x-ray image (e.g., displayed on a video screen) or a digital representation of an x-ray image (e.g., a file corresponding to the pixel output of an x-ray detector). Reference to an "x-ray image" may refer to a single image or a simultaneous or consecutive set of images (as in a stereoscopic imaging system). Reference to an "x-ray image" may also refer to x-ray imaging modalities such as computed tomography (e.g., cone beam CT). The term radiation treatment, as used herein, is the delivery of a prescribed dose of radiation to a pathological anatomy (target) of a patient. Radiation treatment includes radiosurgery (delivery of a few relatively high dose radiation treatments) and radiotherapy (delivery of numerous low dose radiation treatments).

In radiation treatment, often an entire dose of radiation that is to be delivered to a target is not delivered in a single treatment session. To maximize the effect of radiation on cancer, and minimize the effect on healthy tissue, fractionation may be used. Fractionation is a method of radiation treatment in which the total dose of radiation to be delivered to the target is divided into several smaller doses over a period of one or more days. Each individual dose is referred to as a fraction.

Unless stated otherwise as apparent from the following discussion, it will be appreciated that terms such as "processing," "computing," "generating," "comparing" "determining," "setting," "adjusting" or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

One clinical area in which it is important to accurately track the position of a target is radiotherapy or radiosurgery of the prostate to treat prostate cancer. An average patient will experience minimal prostate movement during a radiation treatment session. However, significant prostate motion happens frequently in some patients. Additionally, nearly all patients, in conventional fractionation, experience significant prostate motion in at least some of their fractions. Moderate to significant prostate motion is experienced in about 15% of fractions over the patient population.

FIG. 1 illustrates graphs 100 showing example prostate movement during a radiation treatment session. The graphs 100 include four separate plots that have time along the horizontal axis and prostate position (based on a fiducial center of mass) along the vertical axis. Each plot shows prostate motion in three different directions (superior-inferior, SI; left-right, LR; and anterior-posterior, AP), and a total combined prostate motion (Length).

The upper left plot shows a fraction with minimal prostate motion, which is typical in a majority of fractions (approximately 85%). For these fractions, a diagnostic x-ray imaging frequency of approximately every 1-2 minutes may be sufficient to provide sub-millimeter tracking of the prostate.

The upper right, lower right and lower left plots show typical prostate motion for approximately 15% of fractions. The upper right plot shows a continuous drift of the prostate, which may reflect muscles relaxing and/or a bladder filling during a single fraction. For a relatively slow, steady prostate motion (as illustrated in the upper right plot), an imaging frequency of approximately a diagnostic x-ray image every 30-60 seconds may be sufficient to provide sub-millimeter tracking of the prostate.

The lower right and lower left plots show irregular movement and high-frequency excursions, respectively, that may be a result of, for example, rectal gas. For such rapid prostate motion, it may be necessary to acquire diagnostic x-ray images at a diagnostic imaging frequency of approximately every 15-30 seconds to track the prostate motion with sub-millimeter tracking of the prostate.

Because the prostate is surrounded by radiosensitive structures (e.g., bladder and rectum) susceptible to developing radiation toxicity, it is important to accurately track prostate motion throughout treatment to ensure that a radiation treatment beam is not inadvertently being delivered to areas other than the prostate, and to ensure that adequate doses of radiation are delivered to the prostate. As described above, the imaging frequency that is required to accurately track prostate motion during treatment for different patients can vary dramatically. Moreover, a single patient may show minimal prostate movement during one treatment session, and significant prostate movement during a subsequent treatment session. A patient may also exhibit minimal prostate motion for some of a treatment session, and exhibit significant prostate motion for the remainder of the treatment session. Therefore, it can be important to provide a mechanism both to set the imaging frequency before radiation treatment, and to adjust the imaging frequency during radiation treatment. The general concept is to image as frequently as necessary to track the target accurately (e.g. within a tolerance of 1 mm), but not necessarily as frequently as is possible, because it is desirable to minimize ionizing radiation delivered from the diagnostic imaging. This can be especially important for treatments such as hypofractionated prostate radiosurgery (radiation therapy that gives larger doses, e.g., up to 14 Gy per fraction, in a reduced number of treatment sessions) for at least two reasons: high dose and reduced number of fractions.

Note that radiation treatment of the prostate is described herein for purpose of example. Embodiments of the present invention may equally apply to a broad spectrum of patient anatomies (e.g., organs) within the body that can move. For example, embodiments of the present invention may be applied to treatment of the liver or pancreas, or any other internal target.

Figure 2:
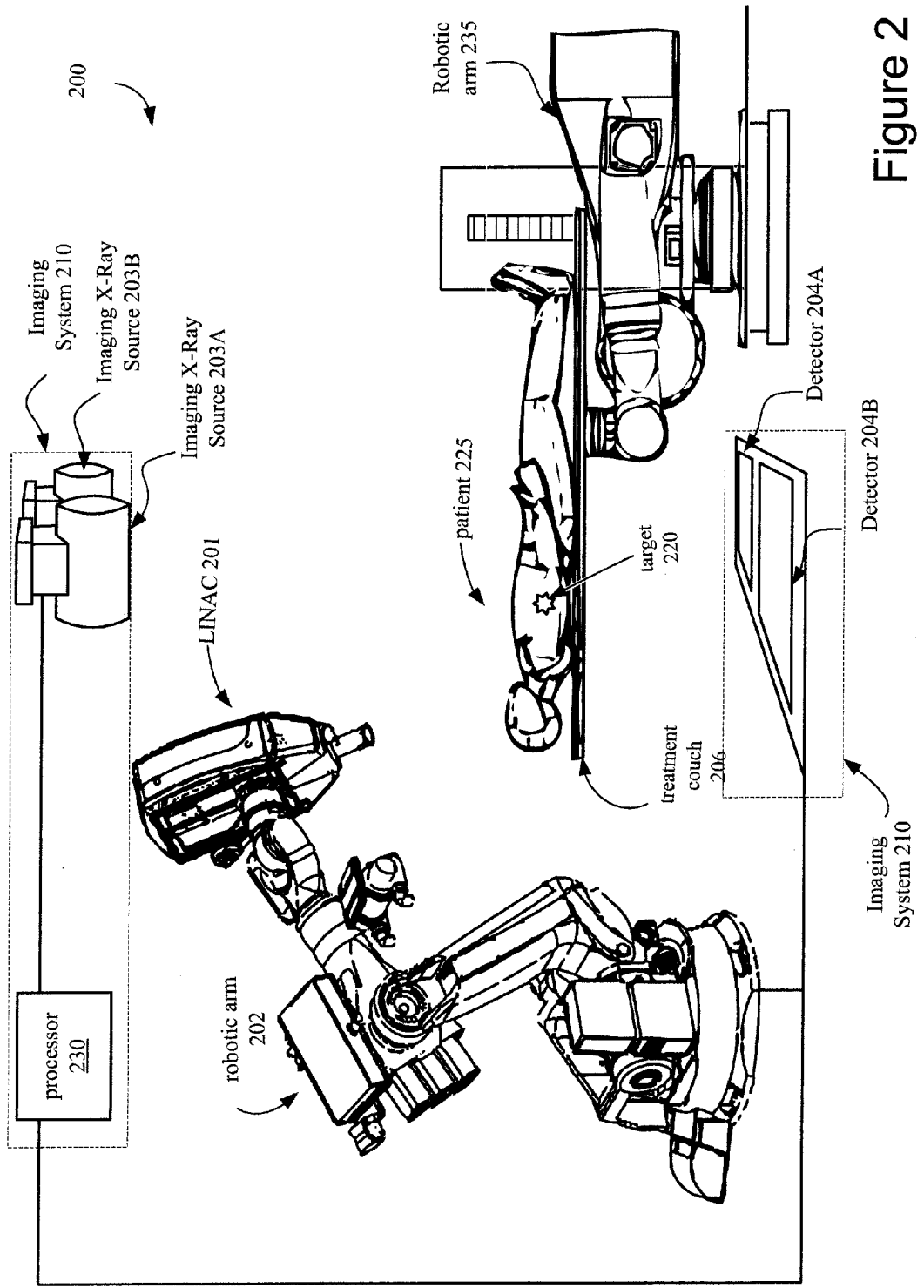
FIG. 2 illustrates a configuration of an image-guided radiation treatment system, in accordance with one embodiment of the present invention.
Figure 3:
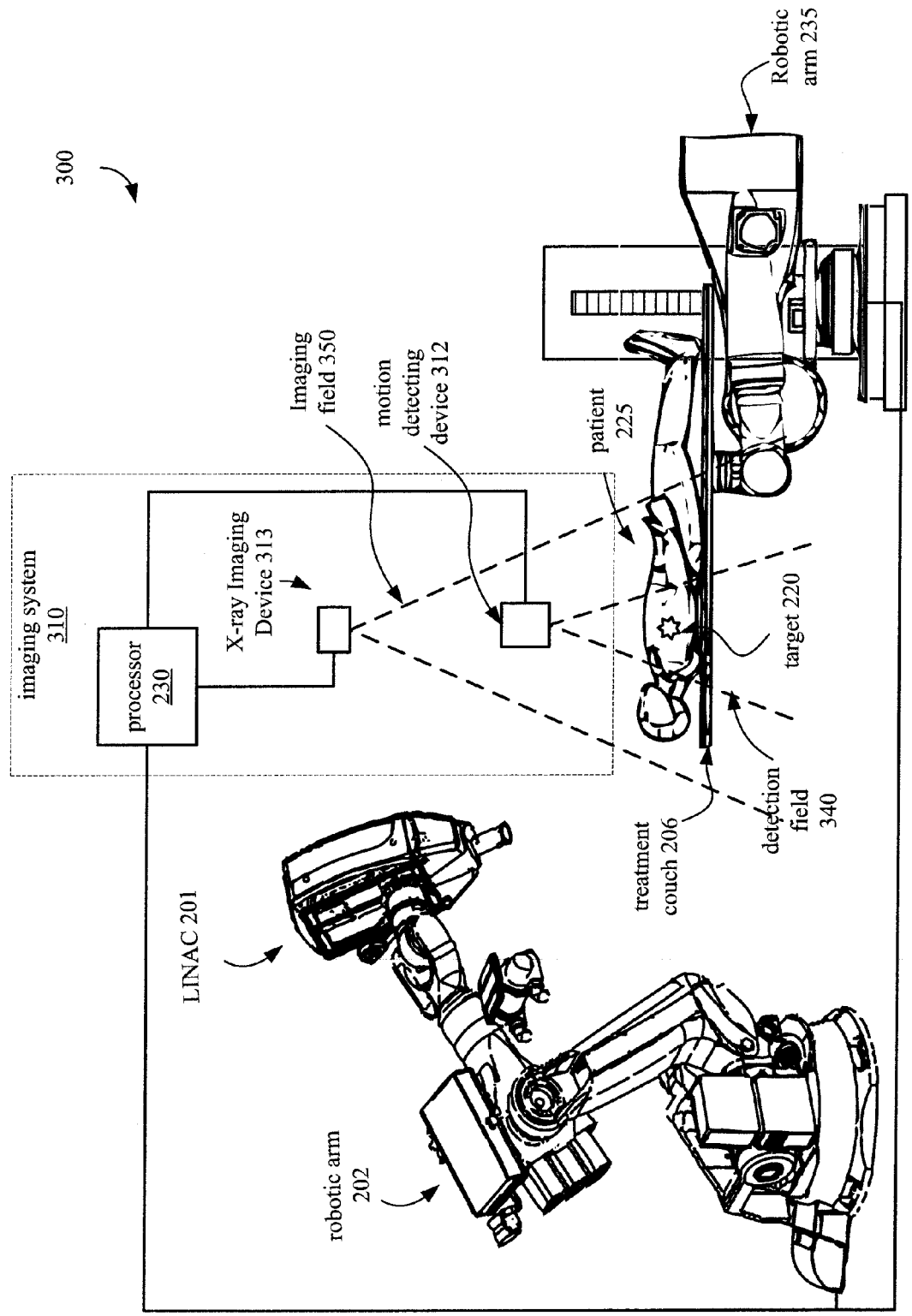
FIG. 3 illustrates a configuration of an image-guided radiation treatment system, in accordance with another embodiment of the present invention.

FIGS. 2 and 3 illustrate configurations of image-guided radiation treatment systems 200 and 300, in accordance with embodiments of the present invention. In the illustrated embodiments, the radiation treatment systems 200 and 300 include a linear accelerator (LINAC) 201 that acts as a radiation treatment source. The LINAC 201 is mounted on the end of a robotic arm 202 having multiple (e.g., 5 or more) degrees of freedom in order to position the LINAC 201 to irradiate a pathological anatomy (e.g., target 220) with beams delivered from many angles, in many planes, in an operating volume around a patient. Treatment may involve beam paths with a single isocenter, multiple isocenters, or with a non-isocentric approach. Alternatively, the LINAC 201 may be mounted on a gantry to provide isocentric beam paths.

The LINAC 201 may be positioned at multiple different nodes (predefined positions at which the robot stops and radiation may be delivered) during treatment by moving the robotic arm 202. At the nodes, the LINAC 201 can deliver one or more radiation treatment beams to a target. The nodes may be arranged in an approximately spherical distribution about a patient. The particular number of nodes and the number of treatment beams applied at each node may vary as a function of the location and type of pathological anatomy to be treated. For example, the number of nodes may vary from 50 to 300, or more preferably 15 to 100 nodes and the number of beams may vary from 200 to 3200, or more preferably 50 to 300.

Referring to FIG. 2, radiation treatment system 200, in accordance with one embodiment of the present invention, includes an imaging system 210 having a processor 230 connected with x-ray sources 203A and 203B and fixed x-ray detectors (imagers) 204A and 204B. Alternatively, the x-ray sources 203A, 203B and/or x-ray detectors 204A, 204B may be mobile, in which case they may be repositioned to maintain alignment with the target 220, or alternatively to image the target from different orientations or to acquire many x-ray images and reconstruct a three-dimensional (3D) cone-beam CT. In one embodiment the x-ray sources are not point sources, but rather x-ray source arrays, as would be appreciated by the skilled artisan. In one embodiment, LINAC 201 serves as an imaging source (whether gantry or robot mounted), where the LINAC power level is reduced to acceptable levels for imaging.

Imaging system 210 may perform computed tomography (CT) such as cone beam CT, and images generated by imaging system 201 may be two-dimensional (2D) or three-dimensional (3D). The two x-ray sources 203A and 203B may be mounted in fixed positions on the ceiling of an operating room and may be aligned to project x-ray imaging beams from two different angular positions (e.g., separated by 90 degrees) to intersect at a machine isocenter (which provides a reference point for positioning the patient on a treatment couch 206 during treatment) and to illuminate imaging planes of respective detectors 204A and 204B after passing through the patient. Imaging system 210, thus, provides stereoscopic imaging of the target 220 and the surrounding volume of interest (VOI). In other embodiments, imaging system 210 may include more or less than two x-ray sources and more or less than two detectors, and any of the detectors may be movable rather than fixed. In yet other embodiments, the positions of the x-ray sources and the detectors may be interchanged. Detectors 204A and 204B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3D CT image based on simulating the x-ray image formation process by casting rays through the CT image.

Imaging system 210 can generate diagnostic x-ray images at a pre-defined imaging frequency for updating a current location of the target. Each diagnostic x-ray image may be compared to the reference image (e.g., corresponding DRR) and/or to previous diagnostic x-ray images to determine present target location and a rate of target movement. If target movement is higher than a predefined tolerance (e.g., 1 mm/min.), the imaging system may increase the imaging frequency to update target location and more accurately direct radiation to the moving target. If target movement is lower than the predefined tolerance, the imaging system 210 may decrease the imaging frequency, as fewer images are necessary to track target movement within the desired tolerances. It will be appreciated that upper and lower predefined tolerances may be selected, thereby defining a range of movement where the imaging frequency is satisfactory, and where the frequency is increased or decreased if movement is above or below (respectively) the upper and lower predefined tolerances. Changing the imaging frequency in response to target movement is discussed in greater detail below with reference to FIGS. 7A and 7B.

Referring to FIG. 3, in alternative embodiments an imaging system 310 includes a motion detection device 312 to determine target motion, the motion detecting device 312 having a detection field 340. If the motion detecting device 312 detects motion that exceeds a treatment tolerance, x-ray imaging device 313 may be directed to generate a new diagnostic x-ray image at a region within an imaging field 350. The motion detecting device 312 can be any sensor or other device capable of identifying target movement. The motion detecting device 312, may be, for example an ultrasound scanner, an optical sensor such as a camera, a pressure sensor, an electromagnetic sensor, or some other sensor that can provide motion detection without delivering ionizing radiation to a user (e.g., a sensor other than an x-ray imaging system). In one embodiment, the motion detecting device 312 acquires measurement data indicative of target motion in real-time. Alternatively, the measurement data may be acquired at a frequency that is higher (potentially substantially higher) than can be achieved or than is desirable with x-ray imaging (due to ionizing radiation delivered to the patient with each x-ray image). In one embodiment, the motion detecting device 312 does not provide a high absolute position accuracy. Instead, the motion detecting device 312 may provide sufficient relative position accuracy to detect patient movement and/or target movement. Such motion detection may trigger the acquisition of an image having high position accuracy (e.g., an x-ray image).

In one embodiment, the motion detecting device 312 is an ultrasound scanner. The ultrasound scanner may include a one-dimensional (1D) array of transducer elements that produces two-dimensional (2D) ultrasound images, or that is mechanically rotated to produce a series of 2D images that are compounded into a 3D image, or a 2D array of transducer elements that produces 3D images. While patient 225 is lying on treatment couch 206, a transducer of the ultrasound scanner may be held in place on the skin surface of patient 225 (or alternatively placed in the rectum, i.e., transrectal ultrasound). The location of the target 220 may be determined as a positional offset between the target 220 and the transducer of the ultrasound scanner. In one embodiment, a transducer or transducers of the ultrasound scanner can be tracked such that detected motion is in the treatment room coordinate system.

In another embodiment, the motion detecting device 312 is an optical system, such as a camera. The optical system may track the position of light-emitting diodes (LEDs) situated on patient 225. Alternatively, the optical system may directly track a surface region of patient 225, as distinguished from tracking LEDs on the patient. There may be a correlation between movement of the target and movement of the LEDs and/or surface region of the patient 225. Based on the correlation, when motion of the LEDs and/or surface region is detected, it can be determined that the target 220 has also moved sufficiently to require another diagnostic x-ray image to precisely determine the location of the target.

In another embodiment, the motion detecting device 312 includes a radio frequency identification (RFID) system having an interrogator that tracks a location of a transponder located on or in patient 225 based on time of flight of a radio frequency (RF) signal. Alternatively, motion detecting device 312 may be some other type of device that is capable of locating a target, such as an electromagnetic coil array or a laser range finder. Other examples of motion detecting devices 312 include strain gauges, piezoelectric sensors, respirometers, etc.

Before a patient undergoes radiation treatment, a radiation treatment plan is typically developed. A radiation treatment plan is a plan for the delivery of radiation treatment beams to the pathological anatomy of the patient from a number of treatment nodes, with one or more beams (having one or more shapes, angles or orientations) being applied from each node. A radiation treatment plan may also call for acquisition of a number and/or timing of intra-treatment diagnostic x-ray images, which are used to track the location of the target;

diagnostic x-ray images are one example of intra-treatment data collected to track the position of the target. For example, and without limitation, diagnostic x-ray images are registered (as known by the skilled artisan) with pre-treatment 3D image data (e.g., CT image, cone-beam CT image, or MR image). Moreover, a radiation treatment plan may include an imaging protocol that identifies, for example, an imaging modality to use (e.g., single x-ray projections, multiple x-ray projections, etc), an imaging algorithm or algorithms to use, whether to track fiducials or patient anatomy, etc.

As noted, the diagnostic image data are used to track the location of the pathological anatomy during the course of delivering radiation thereto. The location of the pathological anatomy is well known immediately after diagnostic image data is obtained and analyzed. As time passes following acquisition and analysis of the diagnostic image data, the location of the pathological anatomy becomes less certain. The pathological anatomy may remain relatively stationary, it may move slightly or it may have dramatic movements, such as the prostate example previously described. The movements can be caused for any of a number of reasons including, without limitation, patient movement, natural shifting due to non-rigidness of the anatomy, or movement of an adjacent piece of anatomy (e.g., bladder filling, rectal gas etc.). In any event, less certainty in the location of the pathological anatomy results in less certainty that the radiation delivered based on the last diagnostic image data is being delivered as planned with the desired accuracy. The amount of time from diagnostic image data acquisition and analysis to the approximate time after completing the delivery of the latest treatment beam is defined as the image age. To better understand image age within the context of this description, one may consider an image age of zero as that time where the system has the most up to date data on target location. As the image age increases, the target location data ages, and may become less reliable depending on how fast the target is moving or how much the target has moved during that time period. In one embodiment, a radiation treatment plan includes an image age threshold that specifies the maximum allowable image age (e.g., at the end of beam delivery) for a diagnostic x-ray image.

Figure 4:
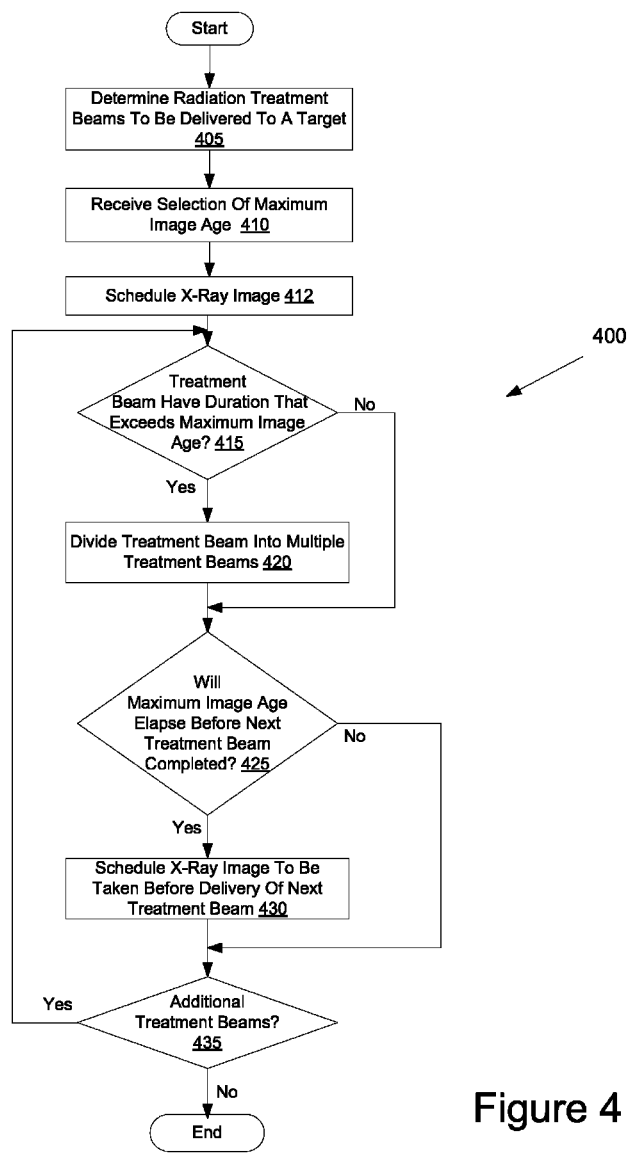
FIG. 4 illustrates a method of developing a radiation treatment plan, in accordance with one embodiment of the present invention.

FIG. 4 illustrates a method 400 of developing a radiation treatment plan, in accordance with one embodiment of the present invention. Method 400 may also adjust a preexisting radiation treatment plan during the treatment. For example, if a clinician selects an image age threshold (maximum allowable image age) before treatment begins or during treatment, method 400 may adjust a preexisting radiation treatment plan based on the image age threshold. In one embodiment, method 400 is performed by a radiation treatment system (e.g., radiation treatment system 200 or 300). Alternatively, method 400 may be performed by a treatment planning system, or by other types of image guided treatment systems.

At block 405, a treatment planning system (or treatment delivery system) determines multiple radiation treatment beams to be delivered to a target (e.g., a pathological anatomy of a patient). Each radiation treatment beam may be delivered from one of many possible nodes. Moreover, each radiation treatment beam may be delivered from a particular orientation at a selected node. For example, a radiation treatment beam may be delivered by a LINAC 201 that is oriented such that it is not aiming at the isocenter.

At block 410, a selection of an image age threshold (maximum allowable image age) is received. Selection of the image age threshold may be received from a clinician, or calculated based on predicted target movement. The selected image age threshold may be based on an expected amount of target movement, based for example on a statistically significant historical sample of patients undergoing the same or similar procedure. For example, a prostate may move a clinically insignificant amount over a period of 10 seconds. Therefore, a maximum image age of 10 seconds may be selected to ensure that movement of the patient/target will not result in unwanted radiation beam delivery to healthy tissue surrounding the prostate. An x-ray imaging frequency and x-ray imaging period may be calculated based on the image age threshold. For example, if the image age threshold is 10 seconds, the calculated x-ray imaging period may be 10 seconds or less. The x-ray imaging frequency dictates the minimum frequency at which diagnostic x-ray images will be taken. The x-ray imaging period dictates the maximum length of time between sequential diagnostic x-ray images, and is the reciprocal of the x-ray imaging frequency. In a further embodiment, the image age threshold defines the x-ray imaging frequency and the x-ray imaging period.

In one embodiment, the imaging system has an inherent maximum sustainable imaging frequency that cannot be exceeded. In a further embodiment, if a diagnostic x-ray image is to be taken at a frequency that is greater than the maximum sustainable imaging frequency, then a delay is introduced so that the maximum sustainable imaging frequency requirement is satisfied. For example, if the maximum sustainable imaging frequency indicates that the diagnostic x-ray images cannot be taken more frequently than every 5 seconds, and a new diagnostic x-ray image is to be taken 2 seconds after a previous x-ray, the new x-ray and treatment may be delayed such that it is taken 5 seconds after the previous x-ray. This may prevent damage to the imaging system.

At block 412, the treatment planning system (or a treatment delivery system) schedules a diagnostic x-ray image to be generated. During treatment, the diagnostic x-ray image may be compared to a previously generated image, such as a DRR or a previous diagnostic x-ray image, to determine a target location before delivering radiation treatment beams. At block 415, the treatment planning system (or the treatment delivery system) determines whether completion of the next radiation treatment beam exceeds the image age threshold, in which case the method proceeds to block 420.

At block 420, the radiation treatment beam is divided into multiple radiation treatment beams. Each of the multiple radiation treatment beams can have an equivalent power level, node position and orientation as the original radiation treatment beam, but have a shorter duration such that each of the multiple treatment beams can be completed within an image age threshold. In one embodiment, the duration of each of the multiple radiation treatment beams is less than the image age threshold. Alternatively, durations of the multiple radiation treatment beams can be selected such that on average the radiation treatment beams are approximately less than or equal to the image age threshold. In such an embodiment, a maximum radiation treatment beam duration may be set such that no radiation treatment beam is longer than the image age threshold by, for example, 20% of the length of the image age threshold. Radiation treatment beams may then have durations of up to 120% of the image age threshold. Radiation treatment beams that would not be completed before 120% of the image age threshold would, therefore, be preceded by a diagnostic x-ray image to ensure a sufficiently low image age, and, therefore, sufficiently high confidence of target location prior to delivery of radiation. Accordingly, a diagnostic x-ray image will not become too old upon which to rely for target location information before delivery of radiation treatment beams.

At block 425, the system determines whether the amount of time that has elapsed since a last diagnostic x-ray image was taken will exceed the image age threshold before a next treatment beam is completed, in which case then a diagnostic x-ray image may become too old to rely upon for determination of a location of the target before delivery of the next radiation treatment beam. If delivery of a treatment beam extends beyond the image age threshold, the target may move beyond a tolerated amount during delivery of the radiation treatment beam, and a portion of the radiation treatment beam may be unintentionally delivered to healthy tissue. If the image age threshold will be exceeded before the next treatment beam is completed, the method proceeds to block 430. Otherwise, the method proceeds to block 435. At block 430, a diagnostic x-ray image is scheduled to be taken before beginning delivery of the next radiation treatment beam. The method then proceeds to block 435. In one embodiment, the duration of the radiation treatment beam includes time that elapses before the treatment beam is actually delivered due to preparation of the treatment beam. Such time is referred to herein as targeting correction overhead, and includes the time that it takes to position the LINAC into a predetermined position and/or orientation (e.g., due to LINAC reposition between nodes and/or within nodes).

At block 435, the treatment planning system (or treatment delivery system) determines whether there are any additional radiation treatment beams included in the treatment plan. If there are additional radiation treatment beams, the method returns to block 415, and the next radiation treatment beam is compared to the image age threshold. Otherwise, the method ends, and the treatment plan may be completed.

Treatment plans may be modified according to method 400 without significantly increasing the duration of patient treatment. Moreover, the final number of diagnostic x-ray images taken of a patient may not be significantly increased over other imaging methodologies (e.g., as compared to a methodology in which a set number of treatment beams are delivered between each diagnostic x-ray image). Consequently, overall radiation exposure to a patient may not increase significantly as a result of implementing method 400, but treatment delivery accuracy is increased. Radiation exposure due to x-ray imaging is discussed in greater detail below with reference to FIG. 8.

Figure 5A:
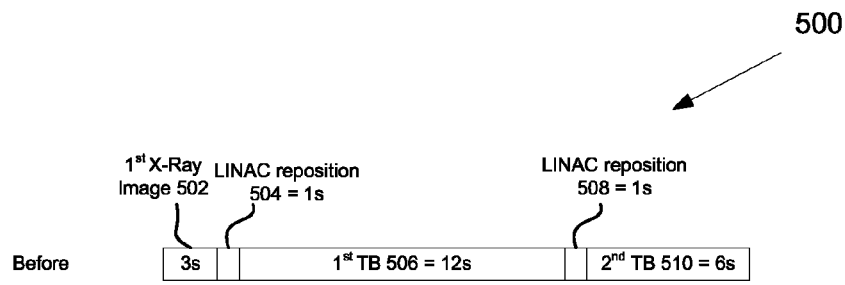
FIGS. 5A-5C illustrate timing diagrams showing a portion of an example treatment plan, in accordance with one embodiment of the present invention.
Figure 5B:
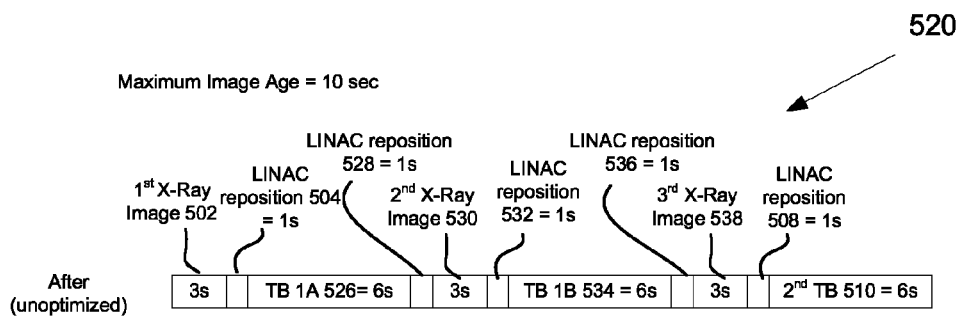
Figure 5C:
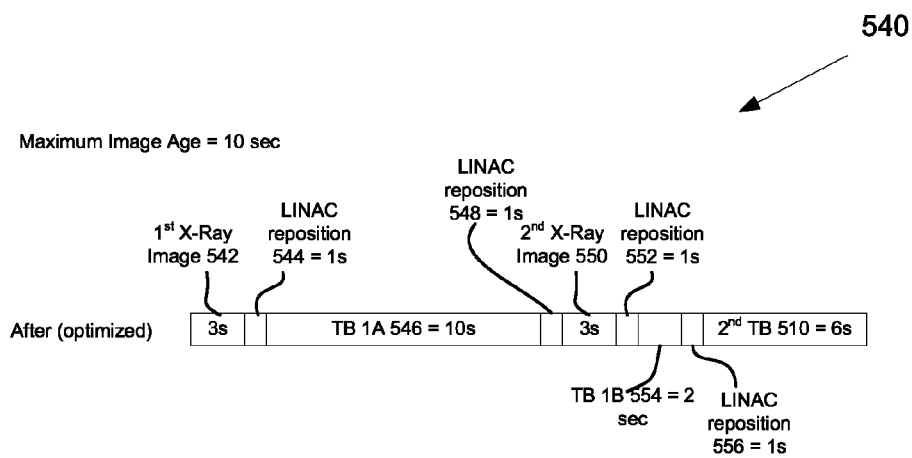

FIGS. 5A-5C illustrate timing diagrams showing a portion of an example treatment plan, in accordance with one embodiment of the present invention. In FIG. 5A, the example treatment plan 500 has not been adjusted by method 400. Treatment plan 500 calls for a diagnostic x-ray image 502 that takes 3 seconds to acquire, followed by LINAC reposition 504 (e.g., motion of the robotic arm that aims a LINAC) that takes 1 second. After the LINAC reposition, a first treatment beam 506 is scheduled to be delivered for 12 seconds, followed by LINAC reposition 508 for another 1 second. A second treatment beam 510 is then to be delivered for six seconds.

FIG. 5B illustrates an example treatment plan 520 corresponding to example treatment plan 500 after it has been adjusted by method 400 based on an image age threshold of 10 seconds, in accordance with one embodiment of the present invention. As shown, the first diagnostic x-ray image 502 and LINAC reposition 504 are unchanged. However, the first treatment beam 506 had a duration that exceeded the image age threshold, and was split into treatment beam 1A 526 and treatment beam 1B 534. Treatment beam 1A 526, having a duration of 6 seconds, is scheduled to be delivered after a first diagnostic x-ray image 502 is taken. If delivery of treatment beam 1B 534 took place immediately after completing delivery of treatment beam 1A 526, then completing delivery of treatment beam 1B 534 would exceed the image age threshold. Therefore, a second diagnostic x-ray image 530 is scheduled to be taken before delivery of treatment beam 1B 534. A third diagnostic x-ray image 538 is scheduled to be taken before delivery of second treatment beam 510 is scheduled to be delivered.

Before the second diagnostic x-ray image 530 and the third diagnostic x-ray image 538 are taken, additional LINAC repositions 528 and 536 are indicated to reposition the LINAC to aim at a treatment isocenter. Such LINAC repositions 528, 536 are a precaution to ensure that the LINAC does not interfere with (e.g., block a portion of) the diagnostic x-ray image. In one embodiment, it may be known which LINAC positions will interfere with x-ray imaging, and motion of the robot may be planned in conjunction with the acquisition of new diagnostic x-ray images to reduce overall treatment time. The skilled artisan will appreciate that all time and time durations provided herein are by way of explanation and not limitation. Longer or shorter times or time durations may be used without exceeding the scope of the present teachings.

FIG. 5C illustrates an example treatment plan 540 corresponding to example treatment plan 500 after it has been adjusted by method 400 based on an image age threshold of 10 seconds, in accordance with another embodiment of the present invention. In FIG. 5C, the first treatment beam 506 has been separated into treatment beam 1A 546, having a duration of 10 seconds, and treatment beam 1B 554, having a duration of 2 seconds. After treatment beam 1A 546 is delivered, a second diagnostic x-ray image 550 is taken. However, unlike the example shown in FIG. 5B, in FIG. 5C both treatment beam 1B 554 and second treatment beam 510 can be delivered before 10 seconds have passed from the time of the second diagnostic x-ray 550. As shown in FIG. 5C, the treatment planning system may divide treatment beams in such a way so as to minimize the number of diagnostic x-ray images needed, which can reduce overall x-ray exposure to a patient.

Figure 6:
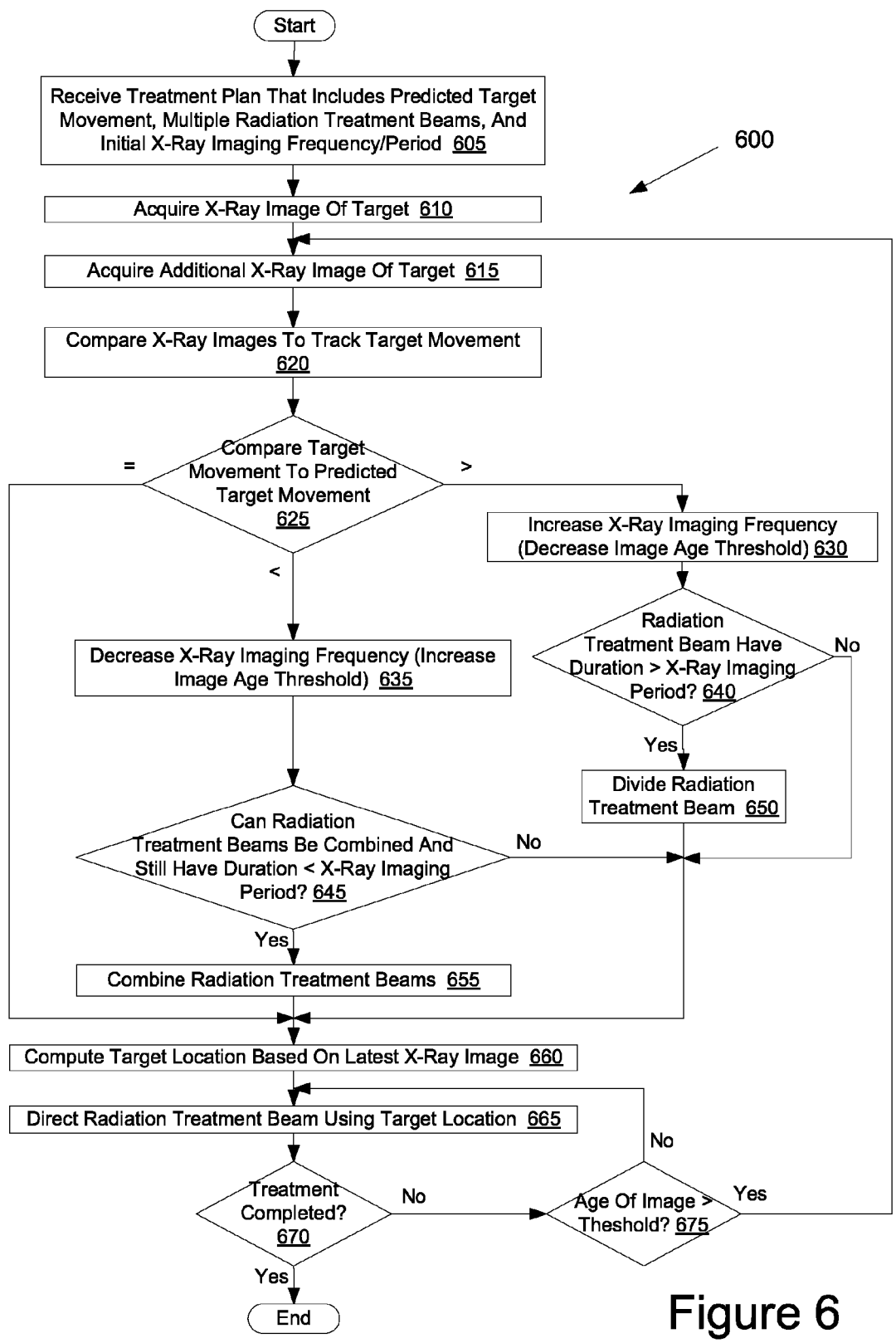
FIG. 6 illustrates one embodiment for a method of controlling the timing for x-ray imaging.

FIG. 6 illustrates one embodiment for a method 600 of controlling the timing for x-ray imaging. In one embodiment, method 600 is performed by radiation treatment system 200 of FIG. 2 or radiation treatment system 300 of FIG. 3. At block 605, a radiation treatment plan that includes predicted target movement, multiple radiation treatment beams, and an initial x-ray imaging frequency/period is received. The initial x-ray imaging frequency/period may be based on an image age threshold. In one embodiment, the x-ray imaging frequency and x-ray imaging period reflect a target x-ray imaging frequency and target x-ray imaging period based on the image age threshold. The actual timing of some diagnostic x-ray images may cause those diagnostic x-ray images to be taken sooner than the x-ray imaging period or later than the x-ray imaging period. Therefore, the actual timing of diagnostic x-ray images may average to the initial x-ray imaging frequency/period. For examples of how a treatment beam may be divided, and when diagnostic x-ray images may be scheduled refer back to FIGS. 5A-5C.

Image guided radiation treatment may be initiated using the received treatment plan. At block 610, a diagnostic x-ray image of the target is acquired. The diagnostic x-ray image may be used to compute a location of the target so as to accurately deliver radiation treatment beams to the target, preferably while avoiding delivering radiation treatment beams to nearby sensitive structures. One or more radiation treatment beams may be delivered subsequent to acquiring the x-ray image of the target.

If the age of the x-ray image will exceed an image age threshold, then an additional diagnostic x-ray image may be acquired prior to delivering any more radiation treatment beams. This can ensure that radiation treatment beams are precise and accurate. At block 615, an additional x-ray image is acquired of the target. At block 620, the imaging system compares the first diagnostic x-ray image to the additional diagnostic x-ray images to track target movement. Differences between the sequential images may be used to register a patient coordinate system with a treatment coordinate system to ensure that the treatment beams are accurately positioned with respect to the pathological anatomy. Differences between the sequential images may be measured using methods known in the art such as feature recognition, pattern intensity matching, etc.

At block 625, it is determined whether the target movement is within a treatment tolerance that is based on a predicted target movement. For example, a certain amount of target movement may be expected and accounted for by the treatment plan. However, if the differences between sequential diagnostic x-ray images indicate an amount of target movement that is different from the expected or planned amount of movement, it may be necessary to adjust the x-ray imaging frequency to better target the radiation beams. Accordingly, if target movement is not within the treatment tolerance (e.g., if the target movement indicated by the differences between the sequential diagnostic x-ray images is greater than the planned or expected target movement during the time interval), the method may proceed to block 630, and the x-ray imaging frequency may be increased (the image age threshold may also be decreased). For example, it may be expected that a patient's prostate will move at a rate of 1 mm per minute, and the x-ray imaging frequency may be initially set such that the prostate will not move more than 1 mm between sequential diagnostic x-ray images. However, if the prostate is detected to have moved more than 1 mm between sequential diagnostic x-ray images, then the x-ray imaging frequency may be increased to ensure that the prostate does not move more than 1 mm between subsequent diagnostic x-ray images. If the time intervals between subsequent diagnostic x-ray images have been decreased, then the total number of diagnostic x-ray images may be increased in response to greater than expected target movement.

In one embodiment, if the target movement is approximately equal to the predicted target movement, then the method proceeds to block 660. If the target movement is less than the predicted target movement the method proceeds to block 635, then the x-ray imaging frequency may be decreased (the image age threshold may also be increased), after which the method proceeds to block 645. If the time intervals between subsequent diagnostic x-ray images have been increased in response to less than expected target movement, then the total number of x-ray images may be decreased.

At block 645, it is determined whether any radiation treatment beams having the same node and orientation can be combined and still complete delivery within the x-ray imaging period (which may be based on the image age threshold). For example, a treatment plan may identify that a particular dose of radiation is to be delivered to the target from a specified position and orientation of the LINAC. Due to the initial x-ray imaging frequency/period, that dose of radiation may be delivered in multiple treatment beams, so that no treatment beam is being delivered to the patient after the image age threshold. Once the x-ray imaging frequency has been decreased, some of these multiple treatment beams may be combined, and still satisfy the image age threshold. To provide an illustration, if the image age threshold were adjusted to 12 seconds in the example described with reference to FIGS. 5A-5C, then the treatment plans 520 and 540 could be revised to resemble treatment plan 500. If treatment beams can be combined the method proceeds to block 655, otherwise the method proceeds to block 660.

At block 640, it is determined whether any radiation treatment beam will complete delivery outside of the x-ray imaging period (extends beyond the image age threshold). If a radiation treatment beam will not complete delivery within the x-ray imaging period, the method proceeds to block 650. Otherwise the method proceeds to block 660.

At block 650, any radiation treatment beam that will complete delivery outside of the x-ray imaging period (extend beyond the image age threshold) is divided into multiple radiation treatment beams. For example, if a radiation treatment beam has a duration that is greater than the x-ray imaging period, it may be divided.

At block 660, the imaging system computes a target location based on the x-ray image or the additional x-ray image. At block 665, the treatment system directs radiation treatment beams using the target location.

At block 670, it is determined whether the treatment has been completed. If the treatment is not yet complete, the method continues to block 675. If the treatment is complete, the method ends.

At block 675, the treatment system determines whether the age of the diagnostic x-ray image will exceed the image age threshold before the time to completion. If the diagnostic x-ray image age will exceed the image age threshold before the time to completion, the method proceeds to block 615, and a new diagnostic x-ray image may be obtained. Otherwise the method proceeds to block 665, and another radiation treatment beam is delivered to the patient.

In one embodiment, rather than computing target movement based on sequential x-ray images, in method 600 target movement may instead be inferred based on detected patient motion. Such patient motion may be detected by an optical scanner that collects image data, a laser range finder, an RFID system, etc. Alternatively, the motion detecting device may measure target motion directly, but may not have a resolution that is high enough to accurately identify the target location for purposes of delivering a radiation treatment beam. For example, the motion detecting device may be an ultrasonic imager that takes ultrasonic images of the target. In such embodiments, at block 615 data other than an x-ray image that is indicative of target motion may be acquired instead of, or in addition to, the x-ray image. In such an embodiment, Block 620 may be skipped, and the data indicative of target motion may be used to determine an amount of target motion.

Figure 7A:
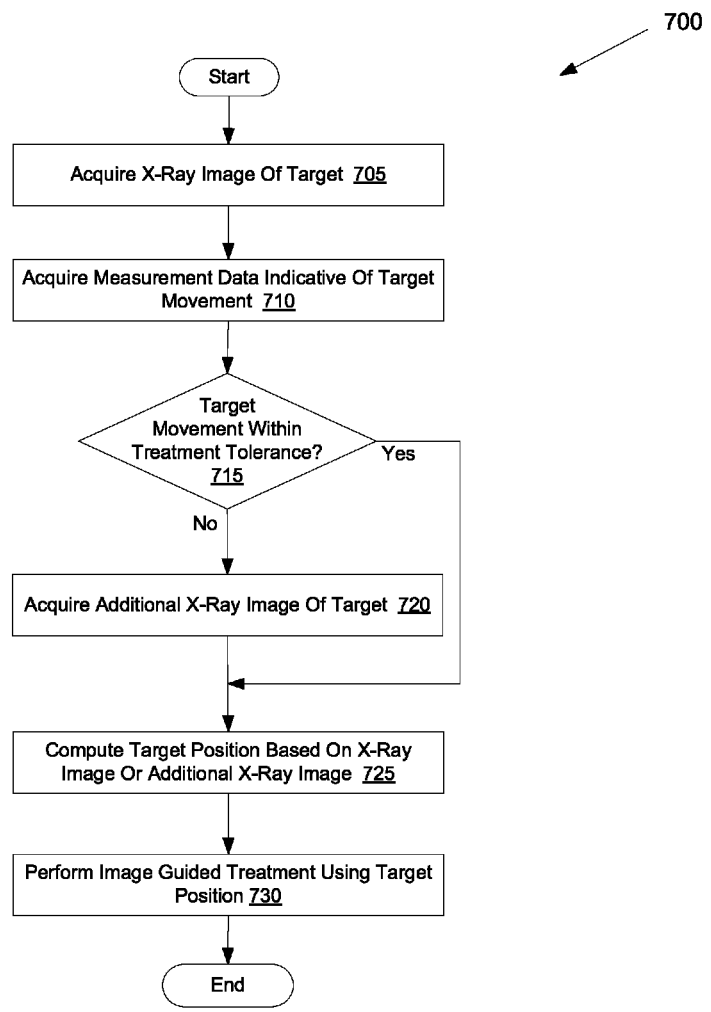
FIG. 7A illustrates another embodiment for a method of controlling the timing for x-ray imaging.

FIG. 7A illustrates another embodiment for a method 700 of controlling the timing for x-ray imaging. Method 700 may control the timing of a single diagnostic x-ray image or of multiple diagnostic x-ray images taken at different times. Where the timing of multiple diagnostic x-ray images is controlled, such control may include controlling an x-ray imaging frequency (and an x-ray imaging period). In one embodiment, method 700 is performed by radiation treatment system 300 or radiation treatment system 200.

At block 705, a diagnostic x-ray image is acquired of a target. At block 710, measurement data indicative of target movement (e.g., a diagnostic x-ray, ultrasound sensor readings, camera readings, etc.) is acquired. The measurement data may be acquired by monitoring the patient with a motion detecting device 313 as described with reference to FIG. 3. Alternatively, the measurement data may be acquired by an imaging system that uses comparisons of sequential diagnostic x-ray images and/or a comparison of current diagnostic x-ray images with pretreatment images to determine whether larger than expected target movement has occurred.

At block 715, target movement is analyzed, and compared to a movement threshold, which may be user selected or predetermined. The target movement may result from a sudden patient movement, such as those due to muscle twitches, spasms (e.g., a cough, sneeze, shudder, etc.), voluntary patient movement (e.g., patient shifting body), or gradual movement (e.g., bladder filling or muscles relaxing). Such patient/target movement may cause enough movement in the target to make the radiation treatment beam to miss the target and hit surrounding healthy tissues and critical structures. If target movement exceeds a movement threshold, then the method proceeds to block 720, and an additional diagnostic x-ray image of the target is acquired. Moreover, if an x-ray imaging frequency is used to control the timing of x-ray imaging, the x-ray imaging frequency may be modified to account for the increased target motion. If the target movement is within the target threshold, the method proceeds to block 725, where the imaging system computes a target position based on the diagnostic x-ray image and/or the additional diagnostic x-ray image. At block 730, a treatment system performs image guided treatment using the target position.

Figure 7B:
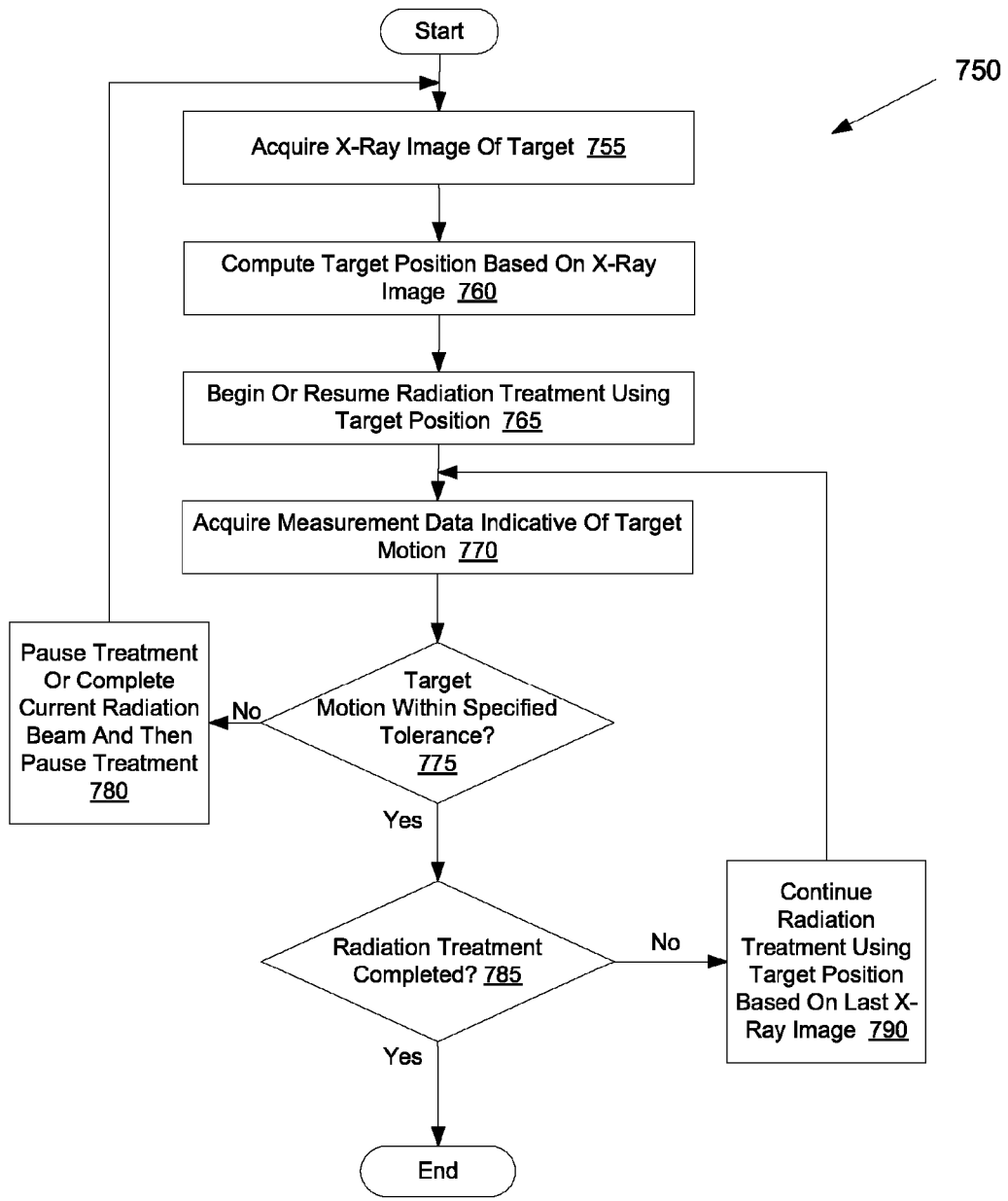
FIG. 7B illustrates yet another embodiment for a method of controlling x-ray imaging.

FIG. 7B illustrates yet another embodiment for a method 750 of controlling x-ray imaging. Method 750 may control the timing of a single diagnostic x-ray image or of multiple diagnostic x-ray images taken at different times. Where the timing of multiple diagnostic x-ray images is controlled, such control may include controlling an x-ray imaging frequency (and an x-ray imaging period). In one embodiment, method 750 is performed by radiation treatment system 300 or radiation treatment system 200.

At block 755, a diagnostic x-ray image is acquired of a target. The x-ray image can be one or more 2D projection x-ray images, a 3D CT image, etc. of the target. At block 760, a position of the target is computed based on the x-ray image. The computed position can be used to accurately determine where to place a radiation treatment beam. At block 765, radiation treatment is begun or resumed based on the computed position of the target.

At block 770, measurement data indicative of target movement is acquired. While treatment is in progress, measurement data indicative of target movement may be continually or periodically acquired. The measurement data may be acquired by an ultrasound sensor, an optical sensor such as a camera, a pressure sensor, a laser range finder, an electromagnetic sensor, or some other sensor that can provide motion detection without delivering ionizing radiation to a user (e.g., a sensor other than an x-ray imaging system). In one embodiment, the measurement data is acquired in real-time by the sensor. Alternatively, the measurement data may be acquired at a frequency that is higher (potentially substantially higher) than can be achieved or than is desirable with x-ray imaging (due to radiation dose delivered to the patient with each x-ray image). In one embodiment, the measurement data does not provide a high absolute position accuracy. Instead, the measurement data may provide sufficient relative position accuracy to detect patient movement and/or target movement.

At block 775, the measurement data is analyzed to determine or estimate a target motion. The measurement data may be a direct measurement of the target motion, or may be a measurement of movement of an external or internal landmark that is indicative of target motion. Examples of external landmarks include, for example, the chest or head of the patient. The target motion is compared to a specified motion threshold, which may be user selected or predetermined. If the target motion exceeds the motion threshold (is outside the specified treatment tolerance), then the method proceeds to block 780. If the target motion does not exceed the motion threshold (is within the specified treatment tolerance), the method proceeds to block 785.

At block 780, the radiation treatment may be paused, or a current radiation treatment beam that is being delivered to the patient may be completed, after which treatment is paused. The method then returns to block 755 to acquire a new x-ray image.

At block 785, the system determines whether radiation treatment has completed. Radiation treatment is complete when all radiation treatment beams for a treatment session have been delivered to the patient. If the radiation treatment has not completed, the method proceeds to block 790, and the radiation treatment continues using the target position that was computed based on the last x-ray image. The method then continues to block 770 to continue acquiring measurement data indicative of target motion. If the radiation treatment has completed, the method ends.

Each diagnostic x-ray image taken of a patient exposes the patient to an amount of radiation. The amount of radiation that a diagnostic x-ray image exposes the patient to depends on the power level of the x-ray source and on the duration of a diagnostic x-ray beam used to generate the diagnostic x-ray image. During image guided treatment, multiple diagnostic x-ray images are typically taken. Therefore, image guided treatment (which may include a single treatment session and/or multiple treatment sessions) may expose the patient to increased levels of radiation. In one embodiment, the amount of radiation that is delivered and that will be delivered to a patient is monitored. If total radiation exposure for a treatment will exceed a radiation exposure threshold, a treatment plan may be adjusted to reduce the total radiation delivered to the patient.

Figure 8:
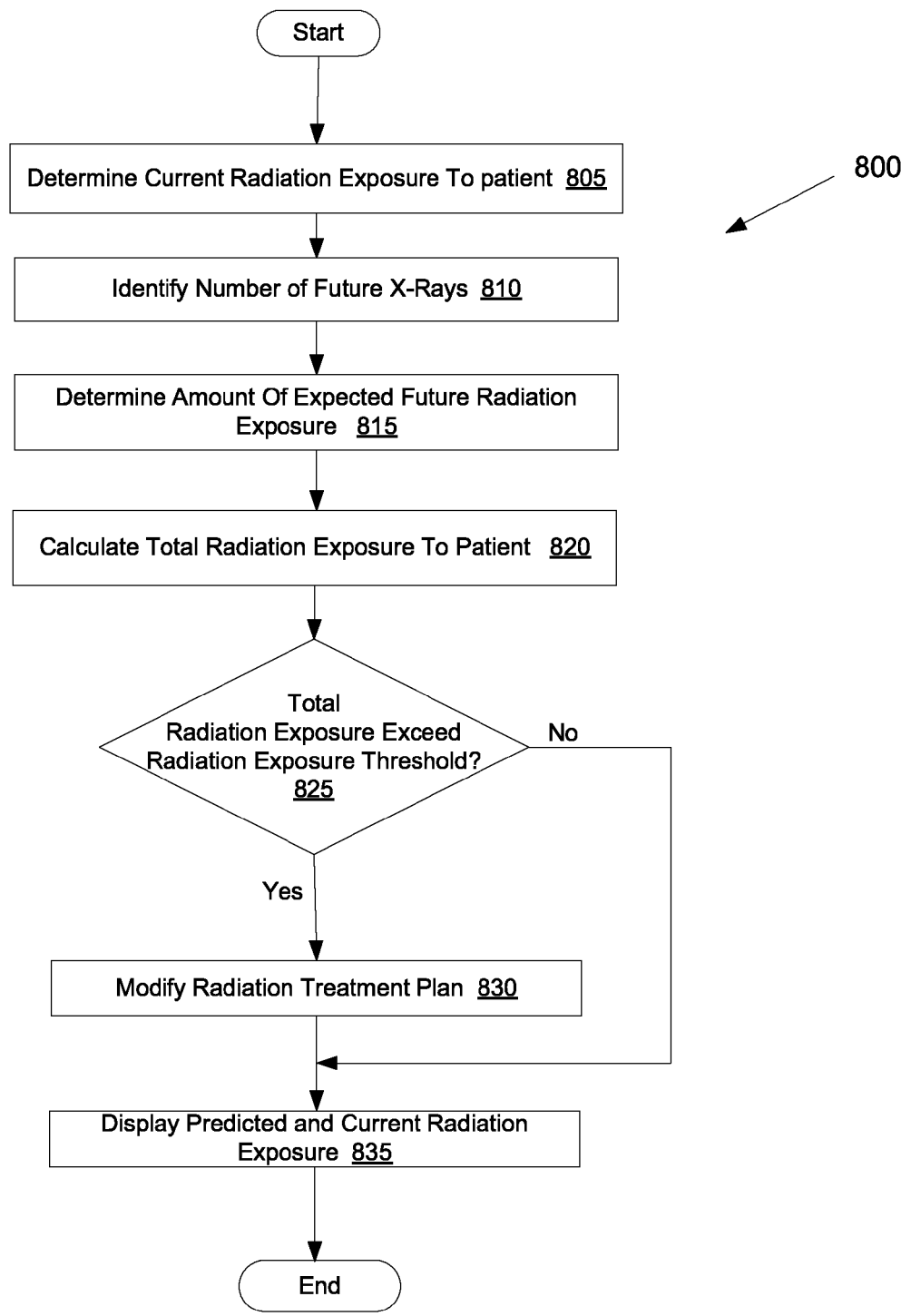
FIG. 8 illustrates one embodiment for a method of monitoring patient radiation exposure.

FIG. 8 illustrates a method 800 of monitoring patient x-ray exposure, in accordance with one embodiment of the present invention. Method 800 may be performed whenever an x-ray imaging frequency or an image age threshold is modified for a radiation treatment plan. Alternatively, method 800 may be performed periodically or continuously to ensure that a patient is not exposed to excessive radiation. In one embodiment, method 800 is performed by radiation treatment system 300 or by radiation treatment system 200.

At block 805, a current radiation treatment exposure of a patient is determined. The current radiation treatment exposure can be determined based on the number of x-rays that the patient has received, and the power and duration of each of the x-rays (i.e., dose delivered to the patient via x-ray imaging). Each of these values may be recorded as diagnostic x-ray images are taken, and/or may be included in a radiation treatment plan for the patient. At block 810, a number of expected future diagnostic x-ray images are identified, and may include all x-rays images that will be delivered to the patient during treatment. Treatment may occur over a period of days or weeks, or may occur in a single day. The number of future x-rays images may be determined by analyzing the number of images scheduled in a radiation treatment plan. Alternatively, the number of future images may be determined based on an x-ray imaging frequency. At block 815, an amount of radiation to be delivered by future x-ray imaging is determined, which can be calculated based on the power level and duration of the future x-ray images. At block 820, the total amount of radiation exposure for the patient is determined by adding the current radiation exposure and the predicted future radiation exposure. At block 825, the total predicted patient radiation exposure is compared to a radiation exposure threshold. If the total predicted radiation exposure exceeds the radiation exposure threshold, the method proceeds to block 830. Otherwise the method ends.

At block 830, a radiation treatment plan for the patient is modified to reduce the amount of radiation to which the patient will be exposed. An example of a modification that can be made to reduce radiation exposure is reducing the imaging frequency to limit the number of x-rays that will be delivered to the patient. In one embodiment, a maximum imaging frequency is set. If a clinician attempts to adjust an imaging frequency beyond the maximum imaging frequency, the clinician may be warned that the patient may be exposed to unhealthy levels of radiation. Alternatively, it may not be possible to exceed the maximum imaging frequency. Another example of a modification that can be made to the image treatment plan to reduce radiation exposure is reducing the power level of diagnostic x-ray images. Other adjustments can also be made, as will be appreciated by the skilled artisan. At block 835, the predicted and current radiation exposure for the patient is displayed. The method then ends.

Figure 9:
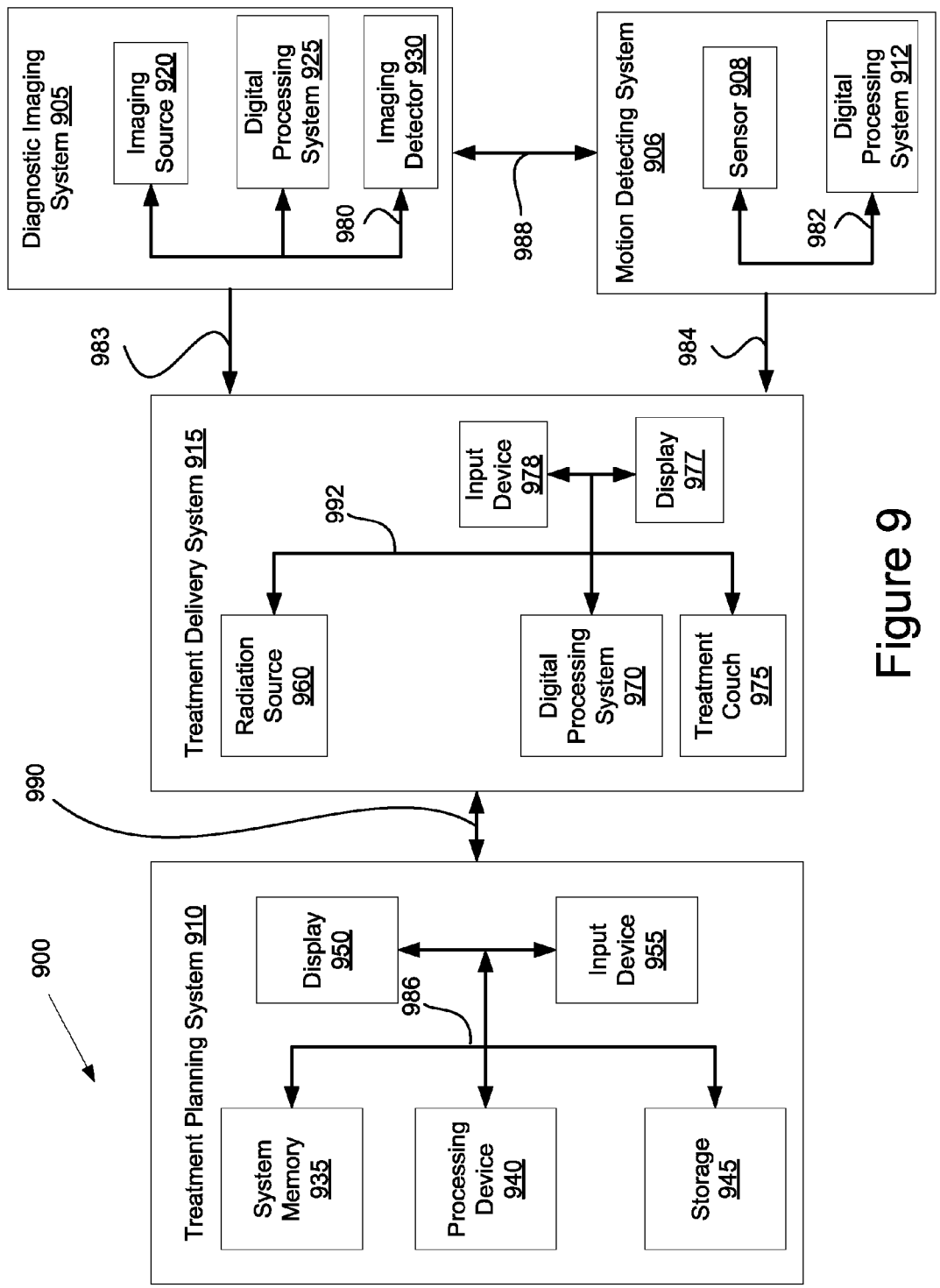
FIG. 9 illustrates one embodiment of systems that may be used in image guided treatment in which features of the present invention may be implemented.

FIG. 9 illustrates one embodiment of systems that may be used in performing radiation treatment in which features of the present invention may be implemented. As described below and illustrated in FIG. 9, a system 900 may include a diagnostic imaging system 905, a treatment planning system 910, a treatment delivery system 915 and a motion detecting system 906. In one embodiment, the diagnostic imaging system 905 and the motion detecting system 906 are combined into a single unit.

Motion detecting system 906 may be any system capable of detecting patient motion and/or target motion. For example, motion detecting system 906 may be a computed tomography (CT) system, an ultrasound system, video camera, or the like. Motion detecting system 906 includes one or more sensors 908 for detecting patient and/or target motion. For example, a video camera may include a lens and array of charge coupled devices (CCDs) for converting incident light into an electrical signal.

The sensor (or sensors) 908 may be coupled to a digital processing system 912 to control the motion detecting operation and process sensor data. Motion detecting system 906 includes a bus or other means 982 for transferring data and commands among digital processing system 912 and sensor 908. Digital processing system 912 may include one or more general-purpose processors (e.g., a microprocessor), special purpose processor such as a digital signal processor (DSP) or other type of device such as a controller or field programmable gate array (FPGA). Digital processing system 912 may also include other components (not shown) such as memory, storage devices, network adapters and the like. Digital processing system 912 may compute target motion. Digital processing system 912 may transmit the target motion to treatment delivery system 915 over a data link 984 or to diagnostic imaging system 905 over data link 988, which may be, for example, direct links, local area network (LAN) links or wide area network (WAN) links such as the Internet. In addition, the information transferred between systems may either be pulled or pushed across the communication medium connecting the systems, such as in a remote diagnosis or treatment planning configuration.

Diagnostic imaging system 905 may be any system capable of producing medical diagnostic images of a patient that may be used for subsequent medical diagnosis, treatment planning and/or treatment delivery. For example, diagnostic imaging system 905 may be a computed tomography (CT) system, a magnetic resonance imaging (MRI) system, a positron emission tomography (PET) system, an ultrasound system or the like. For ease of discussion, diagnostic imaging system 905 may be discussed below at times in relation to a CT x-ray imaging modality. However, other imaging modalities such as those above may also be used.

In one embodiment, diagnostic imaging system 905 includes an imaging source 920 to generate an imaging beam (e.g., x-rays, ultrasonic waves, radio frequency waves, etc.) and an imaging detector 930 to detect and receive the beam generated by imaging source 920, or a secondary beam or emission stimulated by the beam from the imaging source (e.g., in an MRI or PET scan).

The imaging source 920 and the imaging detector 930 may be coupled to a digital processing system 925 to control the imaging operation and process image data. In one embodiment, diagnostic imaging system 905 receives motion data from motion detecting system 906, and determines when to acquire images based on the motion data. In another embodiment, diagnostic imaging system 905 may receive imaging commands from treatment delivery system 915.

Diagnostic imaging system 905 includes a bus or other means 980 for transferring data and commands among digital processing system 925, imaging source 920 and imaging detector 930. Digital processing system 925 may include one or more general-purpose processors (e.g., a microprocessor), special purpose processor such as a digital signal processor (DSP) or other type of device such as a controller or field programmable gate array (FPGA). Digital processing system 925 may also include other components (not shown) such as memory, storage devices, network adapters and the like. Digital processing system 925 may be configured to generate digital diagnostic images in a standard format, such as the DICOM (Digital Imaging and Communications in Medicine) format, for example. In other embodiments, digital processing system 925 may generate other standard or non-standard digital image formats. Digital processing system 925 may transmit diagnostic image files (e.g., the aforementioned DICOM formatted files) to treatment delivery system 915 over a data link 983, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treat a patient despite the existence of a physical separation between the system user and the patient.

Treatment delivery system 915 includes a therapeutic and/or surgical radiation source 960 to administer a prescribed radiation dose to a target volume in conformance with a treatment plan. Treatment delivery system 915 may also include a digital processing system 970 to control radiation source 960, receive and process data from diagnostic imaging system 905 and/or motion detecting system 906, and control a patient support device such as a treatment couch 975. Digital processing system 970 may be configured to register 2D radiographic images received from diagnostic imaging system 905, from two or more stereoscopic projections, with digitally reconstructed radiographs (DRRs) generated by digital processing system 925 in diagnostic imaging system 905 and/or DRRs generated by processing device 940 in treatment planning system 910. Digital processing system 970 may include one or more general-purpose processors (e.g., a microprocessor), special purpose processor such as a digital signal processor (DSP) or other type of device such as a controller or field programmable gate array (FPGA). Digital processing system 970 may also include other components (not shown) such as memory, storage devices, network adapters and the like.

In one embodiment, digital processing system 970 includes system memory that may include a random access memory (RAM), or other dynamic storage devices, coupled to a processing device, for storing information and instructions to be executed by the processing device. The system memory also may be used for storing temporary variables or other intermediate information during execution of instructions by the processing device. The system memory may also include a read only memory (ROM) and/or other static storage device for storing static information and instructions for the processing device.

Digital processing system 970 may also include a storage device, representing one or more storage devices (e.g., a magnetic disk drive or optical disk drive) for storing information and instructions. The storage device may be used for storing instructions for performing the treatment delivery steps discussed herein. Digital processing system 970 may be coupled to radiation source 960 and treatment couch 975 by a bus 992 or other type of control and communication interface.

Digital processing system 970 may implement methods (e.g., such as methods 300 through 800 described above) to manage timing of diagnostic x-ray imaging in order to maintain alignment of a target with a radiation treatment beam delivered by the radiation source 960.

In one embodiment, the treatment delivery system 915 includes an input device 978 and a display 977 connected with digital processing system 970 via bus 992. The display 977 can show trend data that identifies a rate of target movement (e.g., a rate of movement of a target volume that is under treatment). The display can also show a current radiation exposure of a patient and a projected radiation exposure for the patient. The input device 978 can enable a clinician to adjust parameters of a treatment delivery plan during treatment. For example, the clinician may select a new image age threshold or target movement threshold via input device 978.

Treatment planning system 910 includes a processing device 940 to generate and modify treatment plans. Processing device 940 may represent one or more general-purpose processors (e.g., a microprocessor), special purpose processor such as a digital signal processor (DSP) or other type of device such as a controller or field programmable gate array (FPGA). Processing device 940 may be configured to execute instructions for performing treatment planning operations discussed herein.

Treatment planning system 910 may also include system memory 935 that may include a random access memory (RAM), or other dynamic storage devices, coupled to processing device 940 by bus 986, for storing information and instructions to be executed by processing device 940. System memory 935 also may be used for storing temporary variables or other intermediate information during execution of instructions by processing device 940. System memory 935 may also include a read only memory (ROM) and/or other static storage device coupled to bus 986 for storing static information and instructions for processing device 940.

Treatment planning system 910 may also include storage device 945, representing one or more storage devices (e.g., a magnetic disk drive or optical disk drive) coupled to bus 986 for storing information and instructions. Storage device 945 may be used for storing instructions for performing the treatment planning steps discussed herein.

Processing device 940 may also be coupled to a display device 950, such as a cathode ray tube (CRT) or liquid crystal display (LCD), for displaying information (e.g., a 2D or 3D representation of the VOI) to the user. An input device 955, such as a keyboard, may be coupled to processing device 940 for communicating information and/or command selections to processing device 940. One or more other user input devices (e.g., a mouse, a trackball or cursor direction keys) may also be used to communicate directional information, to select commands for processing device 940 and to control cursor movements on display 950.

Treatment planning system 910 may share its database (e.g., data stored in storage 945) with a treatment delivery system, such as treatment delivery system 915, so that it may not be necessary to export from the treatment planning system prior to treatment delivery. Treatment planning system 910 may be linked to treatment delivery system 915 via a data link 990, which may be a direct link, a LAN link or a WAN link.

It should be noted that when data links 983, 984 and 990 are implemented as LAN or WAN connections, any of diagnostic imaging system 905, treatment planning system 910, motion detecting system 906 and/or treatment delivery system 915 may be in decentralized locations such that the systems may be physically remote from each other. Alternatively, any of diagnostic imaging system 905, treatment planning system 910, motion detecting system 906 and/or treatment delivery system 915 may be integrated with each other in one or more systems.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the application of radiation beam(s).

It will be apparent from the foregoing description that aspects of the present invention may be embodied, at least in part, in software. That is, the techniques may be carried out in a computer system or other data processing system in response to its processor, such as digital processing system 970, for example, executing sequences of instructions contained in a memory. In various embodiments, hardware circuitry may be used in combination with software instructions to implement the present invention. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by a processor or controller, such as digital processing system 970.

A machine-readable medium can be used to store software and data which when executed by a data processing system causes the system to perform various methods of the present invention. This executable software and data may be stored in various places including, for example, system memory and storage or any other device that is capable of storing software programs and/or data.

Thus, a machine-readable medium includes any mechanism that provides (i.e., stores and/or transmits) information in a form accessible by a machine (e.g., a computer, network device, personal digital assistant, manufacturing tool, any device with a set of one or more processors, etc.). For example, a machine- readable medium includes recordable/ non-recordable media (e.g., read only memory (ROM); random access memory (RAM); magnetic disk storage media; optical storage media; flash memory devices; etc.), as well as electrical, optical, acoustical or other forms of propagated signals (e.g., carrier waves, infrared signals, digital signals, etc.); etc.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

Certain embodiments may be implemented as a computer program product that may include instructions stored on a computer-readable medium. These instructions may be used to program a general-purpose or special-purpose processor to perform the described operations. A computer-readable medium includes any mechanism for storing or transmitting information in a form (e.g., software, processing application) readable by a computer. The computer-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions.

Additionally, some embodiments may be practiced in distributed computing environments where the computer-readable medium is stored on and/or executed by more than one computer system. In addition, the information transferred between computer systems may either be pulled or pushed across the communication medium connecting the computer systems.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A treatment system, comprising:
    an imaging apparatus;
    a motion detecting apparatus to acquire measurement data indicative of a motion of a target, wherein the motion detecting apparatus comprises an ultrasound apparatus, and wherein the measurement data is ultrasound measurement data;
    a linear accelerator to deliver radiation treatment beams to the target; and
    a processing device coupled with the imaging apparatus, the motion detecting apparatus, and the linear accelerator, wherein the processing device is to:
    direct a first radiation treatment beam to the target; and
    in response to determining that the motion of the target is not within a treatment tolerance:
        cause the imaging apparatus to generate one or more x-ray images of the target, and
        pause the directing of the first radiation treatment beam to the target, wherein the processing device is further to:
    prior to treatment of the target, determine a treatment plan comprising planned delivery of a plurality of radiation treatment beams;
    receive selection of an initial image age threshold;
    determine that completing delivery of at least one radiation treatment beam of the planned delivery of the plurality of radiation treatment beams extends beyond the initial image age threshold; and
    modify the treatment plan by splitting the at least one radiation treatment beam into two or more radiation treatment beams, wherein delivery of each of the two or more radiation treatment beams is completed at or before the initial image age threshold.

2. The treatment system of claim 1, wherein the processing device is further to perform the following, comprising:
    adjust a total number of x-ray images taken during an image guided treatment session in response to the determine of the target motion.

3. A method, comprising:
    prior to treatment of a target, determining a treatment plan that comprises a planned delivery of a plurality of radiation treatment beams;
    directing a first radiation treatment beam of the planned delivery of the plurality of radiation treatment beams to the target using a linear accelerator; and
    in response to determining, using an ultrasound motion detecting apparatus, that a motion of the target is not within a treatment tolerance:
        causing an imaging apparatus to generate one or more x-ray images of the target; and
        pausing the directing of the first radiation treatment beam to the target;
    receiving selection of an initial image age threshold;
    determining that completing delivery of at least one radiation treatment beam of the planned delivery of the plurality of radiation treatment beams extends beyond the initial image age threshold; and
    modifying the treatment plan by splitting the at least one radiation treatment beam into two or more radiation treatment beams, wherein delivery of each of the two or more radiation treatment beams is completed at or before the initial image age threshold.

4. The method of claim 3, further comprising adusting a total number of x-ray images taken during an image guided treatment session in response to the determining of the target motion.

5. A non-transitory machine readable medium having instructions to cause a processing device to perform a following comprising:
    prior to treatment of a target, determine a treatment plan that comprises a planned delivery of a plurality of radiation treatment beams;
    direct a first radiation treatment beam of the planned delivery of the plurality of radiation treatment beams to the target using a linear accelerator; and in response to a motion of the target being determined, using an ultrasound motion detecting apparatus, not to be within a treatment tolerance:
- cause an imaging apparatus to generate one or more x-ray images of the target; and
- pause the directing of the first radiation treatment beam to the target;

receive selection of an initial image age threshold;

determine that completing delivery of at least one radiation treatment beam of the planned delivery of the plurality of radiation treatment beams extends beyond the initial image age threshold; and modify the treatment plan by splitting the at least one radiation treatment beam into two or more radiation treatment beams, wherein delivery of each of the two or more radiation treatment beams is completed at or before the initial image age threshold.

6. The non-transitory machine readable medium of claim 5 having instructions to cause the processing device to further perform the following comprising adjust a total number of x-ray images taken during an image guided treatment session in response to the determining of the target motion.

\* \* \* \* \*